United States Patent [19]

Rosa

[11] Patent Number: 4,642,114
[45] Date of Patent: Feb. 10, 1987

[54] POSTERIOR CHAMBER INTRAOCULAR LENS

[76] Inventor: Daniele S. A. Rosa, 28 Avenue Raphael, 75016 Paris, France

[21] Appl. No.: 726,268

[22] Filed: Apr. 23, 1985

Related U.S. Application Data

[63] Continuation-in-part of Ser. No. 540,796, Oct. 11, 1983, abandoned.

[30] Foreign Application Priority Data

May 16, 1983 [FR] France ................... 83 08037

[51] Int. Cl.$^4$ ............................................. A61F 2/16
[52] U.S. Cl. ........................................................ 623/6
[58] Field of Search ................................ 3/13; 623/6

[56] References Cited

U.S. PATENT DOCUMENTS

| | | | |
|---|---|---|---|
| 4,244,060 | 1/1981 | Hoffer | 3/13 |
| 4,412,359 | 11/1983 | Myers | 3/13 |
| 4,418,431 | 12/1983 | Feaster | 3/13 |
| 4,485,499 | 12/1984 | Castleman | 3/13 |

OTHER PUBLICATIONS

Lens Styles from Cilco (Advertisement Brochure with 6 pages), Cilco, Inc., 1616 13th Ave., Box 1680, Huntington, West VA 25717, pp. 1, 4 and 6 cited, Style SK-4 on p. 4 relied upon, Oct. 1982.
"The Hoffer Ridge Lenses from Cilco, Advertisement from Cilco, Inc., 1616 13th Ave., Box 1680, Huntington, West VA, 6 pages, Mar. 1983.
Kratz/Johnson Laser IOL (Advertisement page), American Medical Optics (Model PC-35), one page, 1983.

Primary Examiner—Ronald L. Frinks
Attorney, Agent, or Firm—Thomas A. O'Rourke

[57] ABSTRACT

A posterior chamber lens implant for a human eye includes a biconvex lens body provided at its rear convex surface at the periphery thereof with discontinuous spacers to space the posterior capsule from the convex rear face of the lens implant in the eye. The spacers are pierced to form a conduit giving permeability between the anterior and posterior chambers of the eye.

1 Claim, 10 Drawing Figures

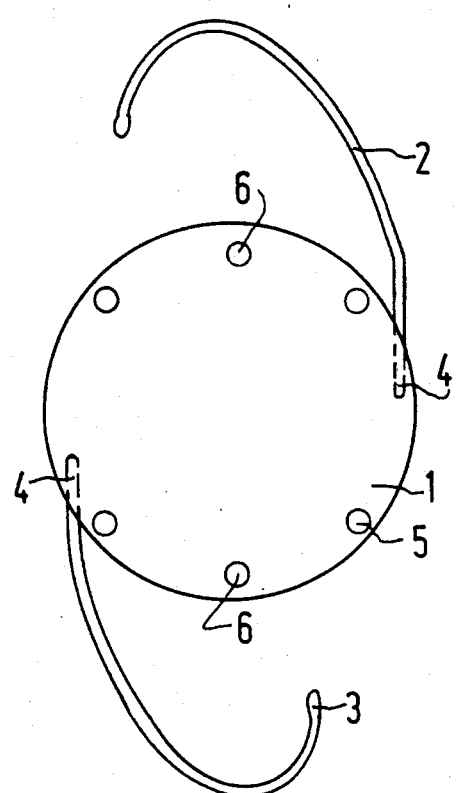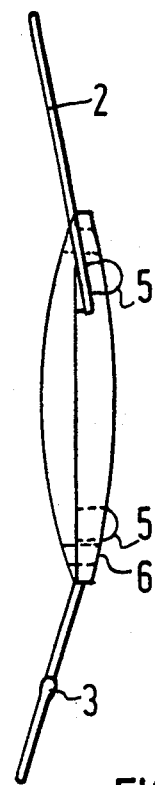
FIG.1　　FIG.2
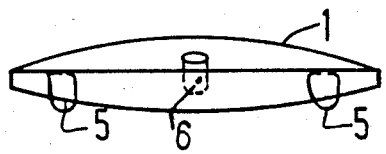
FIG.3

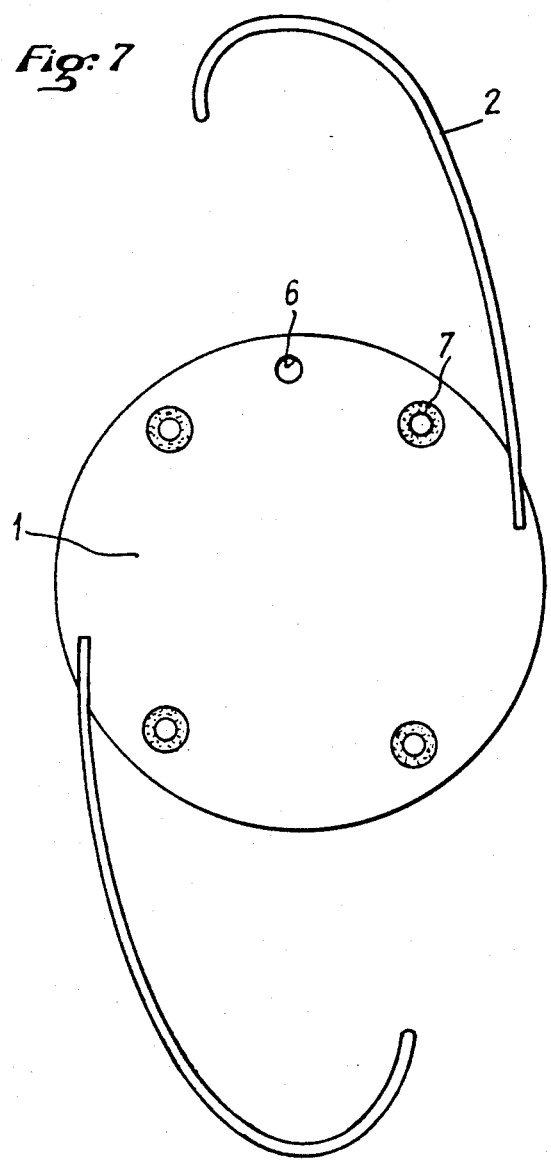
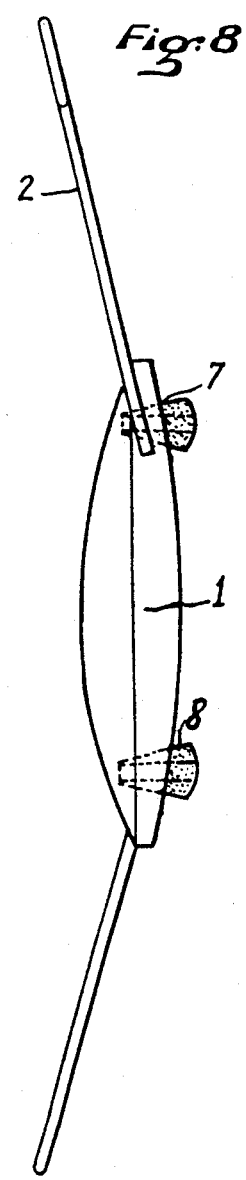
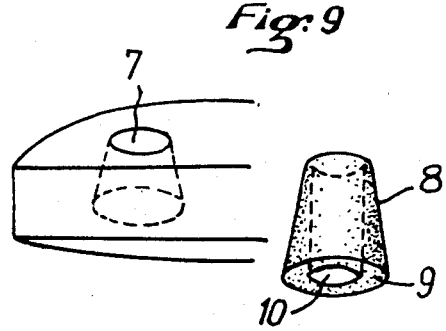

POSTERIOR CHAMBER INTRAOCULAR LENS

CROSS REFERENCE TO A RELATED APPLICATION

This is a continuation-in part of my previous application Ser. No. 540,796 filed on Oct. 11, 1983 now abandoned.

I FIELD OF THE INVENTION

This application relates to a posterior chamber intraocular lens intended for implantation in the capsule of an eye after extracapsular cataract extraction comprising a lens body and haptics extending outwardly from the optic for securing the lens in place in the posterior chamber.

II DESCRIPTION OF THE PRIOR ART

In my former patent No. 4 309 998, I have described a process for cutting biological tissue including transparent tissue, comprising bombarding tissue to be cut with a focussed pulsed laser beam, the power density of the laser being greater than $10^{12}$ Watts/cm$^2$, the beam being passed trough an optical system having a power effect of about 10 diopters. The laser beam being invisible, an auxiliary laser source emitting a marking beam of visible radiation is aligned with the main laser beam, an optical arrangement enabling the divergence of the visible beam to be modified so that the visible focal point coincides with that of the infrared focal point of the YAG laser.( See also the book PULSED YAG LASER SURGERY by SLACK, Incorporated, published 1983).

The known method to perform a posterior capsulotomy or discission consisted in inserting a needle into the eye and to punch a hole behind the lens. U.S. Pat. No. 4,244,060 (Hoffer) describes a special optic having provided on its rear plane face with a continuous circular ridge or lip having a radial opening allowing the discission instrument to pass behind the lens body. So, it is not necessary to disloge the lens body to operate the discission.

In a pamphlet published on March 1983, Kenneth J. HOFFER stated that the ridge disposed on the rear plano face of the lens could be favorable to avoid marking of the rear face of the I.O.L. by the laser beam. Actually, the Hoffer ridge does not provide a totally convenient means to solve the problem of spacing the posterior capsule from the rear face of the lens as far as, especially when the posterior capsule is flaccid or is under pressure of the vitreous humor, the posterior capsule collapses upon the central portion of the rear face. Moreover, the presence of a continuous annular ridge prevents the free communication between the space comprised between the rear face of the lens and the posterior capsule on one hand and the external posterior chamber on the other hand. This structure leads to retropseudophakos blockings ( accumulation of aqueous humors, cristalline material, exsudations and hyaluronic acid if any has been infused for easier implantation at surgery).

From this time, many attempt has been made to allow a capsulotomy of the posterior capsule when this one becomes cloudy and lowers the vision of the eye, by means of a laser beam. The use of a laser beam is non invasive and thus eliminates the possibility of introducing bacteria and other contaminants into the eye. However, there are some risks for injury to the implant during the laser procedures.

The U.S. Pat. No. 4,412,359 discloses a posterior chamber lens implant for use after extracapsular surgery. The lens is of the convex concave type, and the lens is provided with a peripheral ridge for spacing the rear surface of the optic and the posterior capsule. The posterior capsule is so more spaced from the rear surface of the optic than with the Hoffer ridge. However, the distance between the two surfaces (one millimeter for example) is so that impurities can enter the chamber so constituted. In this way, the laser beam can flash on the impurities rather than on the posterior capsule and no discission can be obtained, mainly with a nanosecond laser type, the implant being damaged by the laser beam.

The U.S. Pat. No. 4,485,499 discloses an intraocular lens particularly for implantation in the posterior chamber of an eye after extracapsular extraction particularly for laser surgery. On the rear face are provided rigid roof support members to contact the posterior capsule, the dimensions and spacing of said support members located on the rear face and in the central optical region surrounding the central region in an annular segment defined by a minimum radius of 0.5 mm to a maximum radius of 2.5 mm. The height of the chamber is comprised between 0.1 to 0.6 mm. The location of the support members was found not satisfactorily to maintain all the posterior capsule under pressure of vitreous.

Most implants known from the prior art are planoconvex or convex- concave. Now, during the laser flash, the focusing points of the YAG laser beam and the helium-neon marking beam do not coincide due to the differences of refracting indicia between the YAG laser beam, the wave length of this one being 10.64 nanometers and the wave length of He-Ne laser being about 635 nanometers. In this way, the pointing of the YAG laser is not sufficiently accurate and accidents could occur, marking the implant. If the beams are coincident at the issue of the cornea, they do not coincide after passing through the lens. As a result, the optical breakdown will occur more superficially more near of the rear face of the lens and possibly inside the lens.

One object of the present invention is a YAG compatible implant providing an accurate focussing. Another object of the invention is an implant which does not modify the YAG laser beam geometry.

A further object of the invention is an implant easy to insert, avoiding the so-called windshield, wiper effect resulting in wrinkles of the posterior capsule and which optic does not cause iris iritation by rubbing the posterior face of this iris, causing pigment dispersion and glaucoma, and an optic which keeps the capsule regularly tense and distant from the posterior face of the implant.

DESCRIPTION OF THE INVENTION

These and other objects of the invention are achieved by providing for implantation in the posterior chamber of an eye after extracapsular extraction, an intraocular lens having a particular structure configuration presently to be described enabling subsequent non-invasive post operative surgery, especially Q-switched or mode-locked YAG-laser capsulotomy or other surgery as stated in my previous patent No. 4,309,998.

According to the present invention, the posterior chamber lens implant for a human eye for use after extracapsular surgery in which a posterior capsule is left substantially intact, said lens comprises a substantially circular rigid optic having a front surface, a rear surface and a substantially circular and continuous outer rear edge, said front surface being a continuous convex surface and said rear surface being a continuous convex surface extending between said outer rear edge, said rear convex surface being provided at its periphery with discontinuous spacing means to space the posterior capsule from the convex rear face.

According to another feature of the invention, the curvature radius of the rear face is about 3.5 times the curvature radius of the front face.

So, the posterior chamber defined by the rear surface of the lens and the posterior capsule is of variable depth. The marking beam and the YAG-laser beam have sensibly coincident focussing points and the laser shoot can be effected safely. The focusing point of the YAG-laser beam is pushed towards the rear portion of the eye. The optical breakdown can be shortened in the antero-posterior direction, which makes it possible to reduce wasting of the beam. This reduction leads to minimize the reduction of energy necessary to obtain the desired capsulotomy. Actually, the power of each lens is variable but the above defined relation between the radii of the front and rear surface of the lens were found convenient.

According to another feature of the invention, the diameter of the external rear edge is comprised between 6.3 and 7 millimeters. Lenses according to this feature were found easy to implant and showing a good stability.

So, the distance between the rear surface of the lens and the posterior capsule varies from 0.25–0.3 mm. in the central optical region to 0.35–0.4 mm at the periphery of the lens.

BRIEF DESCRIPTION OF THE DRAWINGS

Three embodiements of the invention are described by way of example only with references to the accompanying drawings, in which:

FIGS. 1 to 3 are three mutually orthogonal views of a first implant in accordance with the invention;

FIG. 7 to 9 are similar views of a third implant;

DESCRIPTION OF PREFERRED EMBODIMENTS AND BEST MODES FOR PRACTISING THE INVENTION

Figure 4:
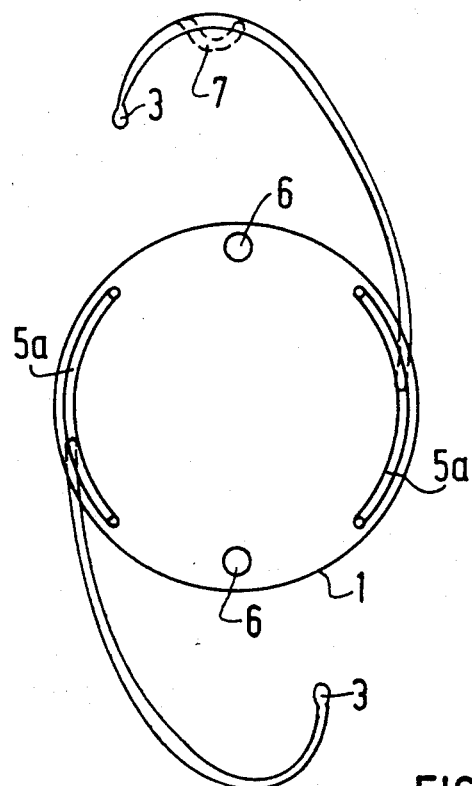
FIGS. 4 to 6 are similar views of a second implant.

The following description concerns preferred embodiments of the invention for purpose of illustration of said invention. Thus this description is not to be taken in a limiting sense.

In the examples, the implant comprises a lens having a convex front face and a rear face, i.e. the face facing the rear of the eye, which is convex, the curvature radius of the rear face being sensibly equal to 3.5 times the curvature radius of the front face. This structure corresponds, on one hand, to physiological requirements for focusing on the retina and, on the other hand, to the necessity of having a same focusing point for the YAG-laser and for the red marking laser slightly behind the posterior capsule. The lens is made of relatively flexible plastic material such as polymethyl methacrylate (PMMA) or "Perspex" (Registered Trademark). The lens has an outer diameter comprised between 6.3 and 7 millimeters and preferably 6.5 mm. It is fixed in the posterior chamber of the eye by means of two retaining loops which are fitted to the rear surface of the lens or which continue from the optic so constituting a one piece PMMA lens. Preferably, the loops are fitted or formed in such a manner that they are forwardly inclined or substantially 10° from the mid plane of the lens. If the implant is a one piece PMMA, the total horizontal width of the lens with the loops should not exceed 7.2 mm. The inclination of the loops could be provided either by a continuous slope inclinated 10° or with step loops. On the one piece PMMA, the spacers should be displaced and moved towards a circumferential foot plate which provides the haptics so leaving a free 5 mm. width optic path.

FIGS. 1 to 3 show a first embodiment of the invention which comprises a biconvex lens 1 of 6.3 mm. diameter and having two retaining loops 2 projecting from the rear face of the lens. The loops 2 are made of 0.2 mm diameter prolene or perspex filaments and are terminated by respective olive-shaped knobs 3. They must have excellent surface state in order to avoid irritation of the ciliary body. The loops 2 are "Sinskey" style loops and they are inclined forwardly from the plane of the implant by an angle of about 10°. In a manner known per se, the lens 1 has at least two diametrically opposed positioning holes 6 defining the 6 o'clock and the 12 o'clock positions. The diameter of these holes is at least 0.2 mm and not more than 0.4 mm. Four smoothly rounded studs 5 project from the rear face of the lens 2. The studs 5 are evenly distributed around the periphery of the lens in between the holes 6, and they are 0.4 mm in diameter and 0.4 mm tall, for example. This arrangement serves to hold off the posterior capsule of the natural lens leaving a space between the capsule and the artificial lens. This space combined with the optic design has proved sufficient to enable a capsulotomy to be performed by means of a pico- or nano-second pulsed laser beam emitted from a neodymium doped YAG (Yttrium-Aluminum-Garnet) laser, without making indelible marks on the implant.

In both embodiments described, the ends 4 of the loops 2 are force fitted into lateral cavities formed in the lens 1. The total length of each loop is at least 13 mm and not more than 14.5 mm.

Figure 5:
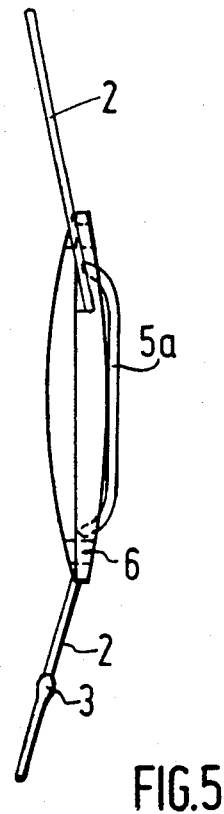
Figure 6:
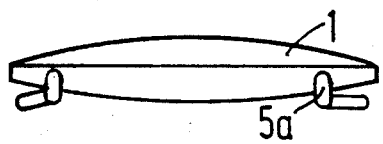

FIGS. 4 to 6 show a second embodiment in which many of the above-described items, in particular the lens 1, the retaining loops 2 and the positioning holes 6, are also to be found. The positioning holes 6 are located 0.2 mm in from the rim of the lens and they are used to adjust the position of the lens in the ocular cavity. In the second embodiment, the posterior capsule is held off the lens by arc means 5a which project from the rear face of the lens 1 instead of the studs 5. The arcs 5a may be made of prolene or perspex filament and they should be flexible and resilient so as to hold off and keep taut the posterior capsule at a distance of 0.4 mm from the lens, thereby enabling a secondary cataract to be treated by laser beam without damaging the implant. The retaining loops 2 may be "Sinskey" type loops as already described or else "J" type loops in which the upper loop has a hook 7 (shown in dashed lines) on the 6 o'clock—12 o'clock axis as defined by the positioning holes 6 to enable the loop to be grasped and bent down to the 12 o'clock positioning hole 6 while the implant is being inserted. A button hole could alternatively be provided in the upper retaining loop for the same purpose.

Each of the arcs 5a is made from 0.2 mm diameter filament which has both ends received in the rear face of the lens 1. Both ends of the filament begin by projecting perpendicularly from the rear face of the lens, and thereafter the filament curves over to form an arc of about 90° running adjacent to the periphery of the lens and in a plane which is parallel to the plane of the lens. The arc is spaced from the rear face of the lens so as to hold the capsule taut a distance of 0.4 mm from the rear face.

FIGS. 7 to 9 show a third embodiement, FIGS. 7 and 8 being two orthogonal views of the implant and FIG. 9 showing the fitting of the prongs or pegs. The lens 1 is provided in addition to the 6 o'clock positioning hole with four positioning holes 7 arranged according to a square, sensibly in the 11, 1, 5, 7 o'clock directions. Each hole 7 has a sensibly frustoconical cross section with a front diameter of 0.3 mm. and a rear diameter of 0.45 to 0.65 millimeters. The positioning holes have a diameter of 0.3 millimeters. Inside the positioning holes 7, are fitted frustoconical pegs or prongs 8, the height of which being greater of 0.3 to 0.4 millimeters than the thickness of the lens at the place where the holes are provided. The external edges of the holes 7 are spaced from the edge by the lens of about 0.1 to 1.5 millimeter. The prongs 8 have a smooth basis surface 9. They are pierced by a central conduit 10, the diameter of which being 0.3 millimeters giving permeability between the anterior and posterior chambers. Due to the frustoconical design of the prongs, the mechanical link is automatically ensured. Preferably, the loop length is comprised between 14 and 14.5 millimeters in view of avoiding discenterings. As before, the haptics are inclined in the front direction at about 10° in relationship with the medial plane of the lens. This inclination aims to avoid that the lens bear on the iris, even if the haptics lie inside the ciliary sulcus. As before, the haptic is provided with a hook (not shown) allowing to replace the implant after luxation if any.

In all the embodiments, the external diameter of the lens 1 is comprised between 6.3 and 7 millimeters and, preferably, is equal to 6.5 millimeters. Now, usually, the lens has an external diameter of 6 millimeters but, due to the presence of the indentations spacing means, the lens becomes unstable and shows a tendency to slide on the posterior capsule giving the winshield wiper syndrom. If the outer diameter of the lens is greater than 7.3 millimeters, the insertion in the posterior chamber needs to have an iris dilatation and becomes very difficult.

As mentioned before, the posterior capsule is stretched on the indentations spacing means. A laser flash operation gives a discontinuous line of impacts. With a square pattern of spacing means, said means constitute a set of references allowing to cut the capsule along medial lines. So, less impact points are necessary for obtaining an opening perfectly axial, vertical or horizontal, which does not lead to drawbacks for the path of the visual axis.

The twelve o'clock hole 6 constitutes a means to grasp the lens and to introduce it in the posterior chamber with a special gripper allowing the catch with only one hand the lens and the superior haptic 2 in folded position.

Figure 10:
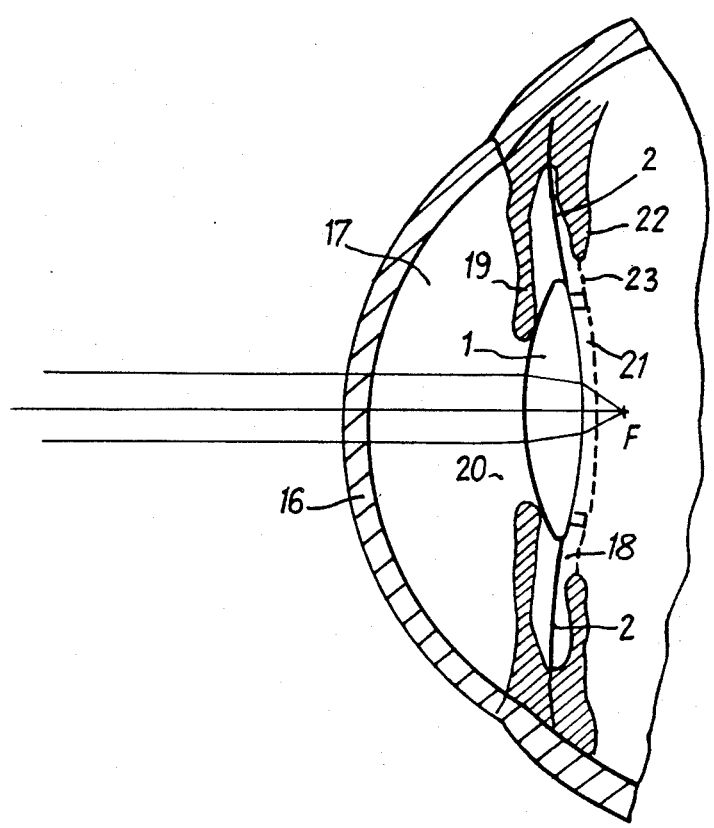
FIG. 10 an implant according the invention in position in a posterior chamber.

The FIG. 10 shows an I.O.L according to the invention after mounting inside an eye. It is possible to recognize the transparent cornea 16, the anterior chamber 17, the pupil 20 in the middle of the iris 19, the posterior chamber 18 and in dash line the posterior capsule 21 linked to the ciliary sulcus by zonular fibers 23. As explained hereabove, the convexity of the rear surface of the lens 1 allows to have coincident focussing points despite the difference of optical path in the lens due to the difference of the wavelengths. On the FIG. 10, the coincident focusing points of both marking laser beam and YAG laser beam are referred to a F. It is situated at about 0.3 millimeter behind the posterior capsule in the central optical area. By delivering ultrashort pulses in the nano to picosecond range concentrated in a small area at the laser focus, enormous power density can be obtained. Optical breakdown takes place producing a centrifugal shock wave and, pratically, no heat is propagated. Mechanical disruption of the target tissue occurs. Simultaneously, the optical breakdown develops atoms at the area of the laser focus which are dissociated into ions and electrons. The high electron density reflect back the 1064 nanometers wavelength of the YAG affording relative protection of the retina when working in the anterior segment.

As it appears from the FIG. 10, the posterior capsule 21 is stretched on the spacing means 8 and this feature has for result to delay the development of secondary cataracts.

Naturally, numerous modifications can be made to the implant while remaining within the scope of the present invention. In particular, the retaining loops may be other designs.

The invention, accordingly, should be taken as defined by the following claims.

What I claim is:

1. A posterior chamber lens implant for a human eye for use after extracapsular surgery in which a posterior capsule is left substantially intact, said lens comprises a substantially circular rigid optic having a front surface, a rear surface and a substantially circular and continuous outer rear edge, said front surface being a continuous convex surface and said rear surface being a continuous convex surface extending between said outer rear edge, said rear convex surface being provided only at its periphery with discontinuous spacing means to space the posterior capsule from the convex rear face and wherein the curvature radius of said rear face is about 3.5 times the curvature radius of the front face and wherein the external diameter of the lens is between 6.3 and 7 millimeters and wherein said implant has at least two retaining loops fitted thereto to engage the ciliary sulcus of the lens bag, said retaining loops being forwardly inclined at an angle of about 10° from the mid plane of the lens and wherein the spacing means comprise four prongs of frustoconical shape fitted in four holes arranged in a square pattern extending through the optic between said front and rear convex surfaces, said prongs being pierced to form conduits giving permeability between said convex surfaces and the anterior and posterior chambers when said lens implant is implanted within an eye.

* * * * *